United States Patent [19]
Kafesjian et al.

[11] 4,017,911
[45] Apr. 19, 1977

[54] HEART VALVE WITH A SINTERED POROUS SURFACE

[75] Inventors: Ralph R. Kafesjian, Irvine; Norman G. Masse, Newport Beach; David P. Keller, Mission Viejo, all of Calif.

[73] Assignee: American Hospital Supply Corporation, Evanston, Ill.

[22] Filed: June 3, 1976

[21] Appl. No.: 692,428

Related U.S. Application Data

[63] Continuation of Ser. No. 473,748, May 28, 1974, abandoned.

[52] U.S. Cl. .......................................... 3/1.5; 3/1.9; 128/92 C; 428/548
[51] Int. Cl.² .......................................... A61F 1/22
[58] Field of Search ............... 128/92 C; 3/1.5, 1.9, 3/1.9 B; 29/182.2, 182.3; 75/208 R, 200, 222

[56] References Cited
UNITED STATES PATENTS

| | | | |
|---|---|---|---|
| 3,471,287 | 10/1969 | Roberts | 75/222 |
| 3,689,942 | 9/1972 | Rapp | 3/1.5 |
| 3,723,996 | 4/1973 | Raible et al. | 3/1.5 |
| 3,852,045 | 12/1974 | Wheeler et al. | 75/222 |

*Primary Examiner*—Brooks H. Hunt
*Attorney, Agent, or Firm*—Lee R. Schermerhorn

[57] ABSTRACT

A unique sintering method of developing a controlled porosity, controlled thickness, metal layer on a metal substrate is disclosed. The region to be coated is cleaned, a suitable adhesive applied and appropriate metal powder poured on. Additional layers of adhesive and powder can be applied to give desired thickness. Pore size is determined by the size and shape of the powder particles and by the degree of sintering selected. Controlled sintering of the particles is carried out at a temperature near the melting point of the metal in a hydrogen atmosphere to permanently attach the particles to the substrate. The sintering is only sufficient to bond the particles while avoiding over-sintering which would close the porosity. No foreign material is left, the adhesive being burned off during sintering. The porous surface thus produced provides secure anchorage for the ingrowth of body tissue in a prosthetic device such as a heart valve or bone implant.

4 Claims, 5 Drawing Figures

U.S. Patent  April 19, 1977  Sheet 1 of 2  4,017,911
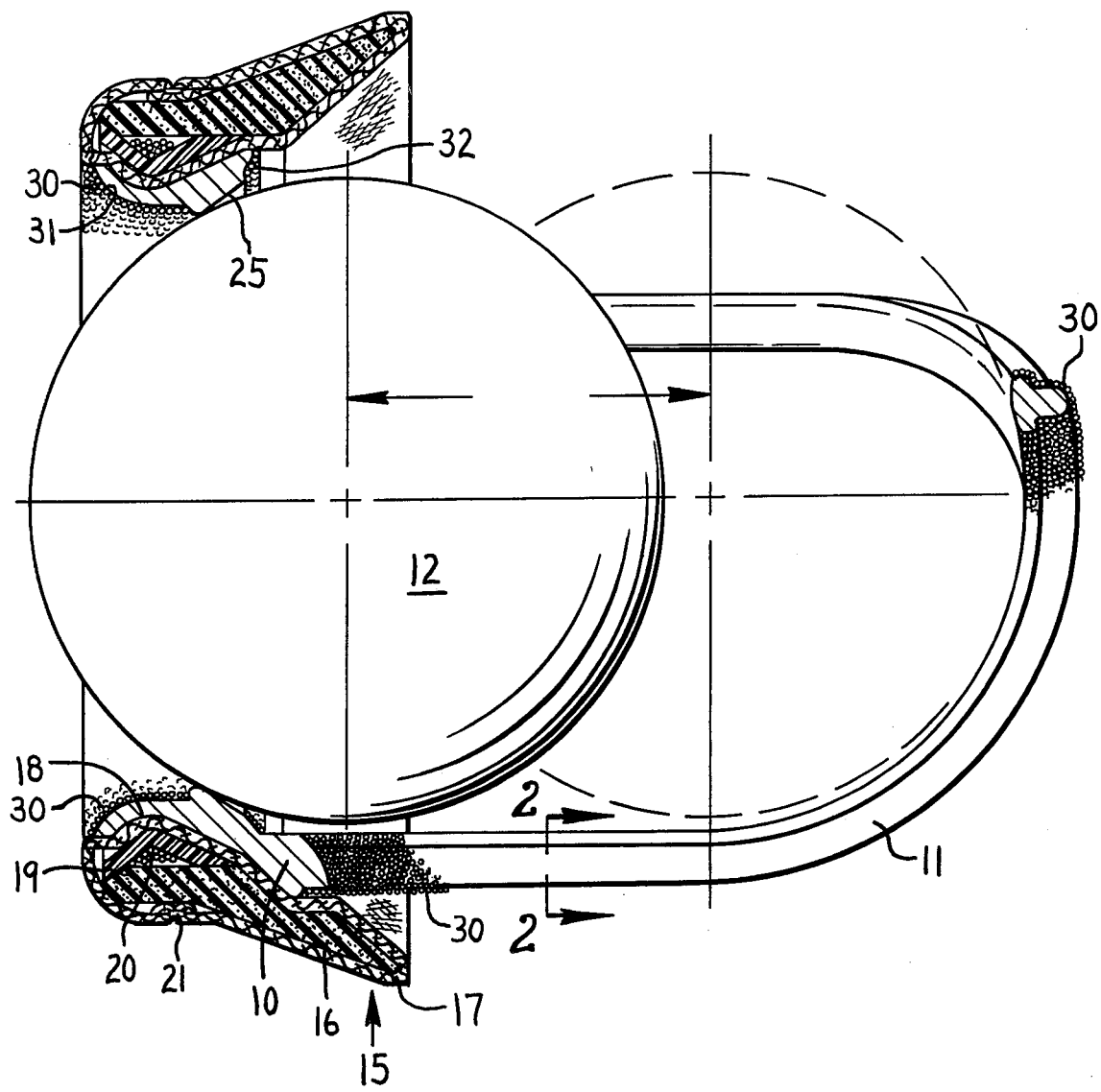
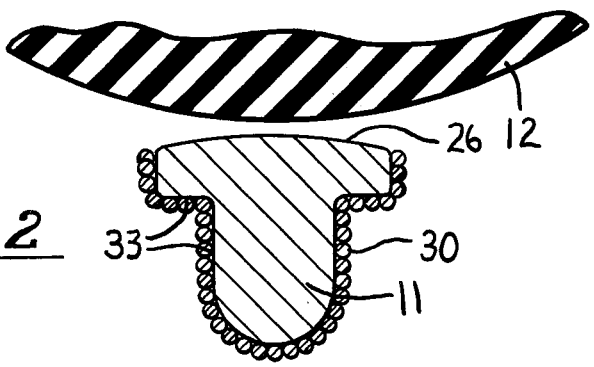

HEART VALVE WITH A SINTERED POROUS SURFACE

CROSS REFERENCE TO RELATED APPLICATION

This application is a continuation of Ser. No. 473,748 filed May 28, 1974.

BACKGROUND OF THE INVENTION

This invention relates to a method of applying a porous metal coating to a metal substrate, and to a substrate, such as a heart valve or other prosthesis, having such a coating.

The anchoring of body tissue to certain synthetic implants in the body is desirable. Metals are used extensively in a variety of implant forms, such as artificial heart valves, hip joints, etc., making it necessary to anchor the body tissue to a metal structure.

The incidence of thrombo embolism poses a continual threat to patients who have undergone surgery for prosthetic heart valve replacement. Clinical evidence has shown that the incidence of thrombo embolism can be significantly decreased within one year after surgery if the prosthetic valve can be constructed to encourage a controlled tissue ingrowth over the surface of the valve exposed to the blood stream. This requires a porous surface.

The most commonly used technique for encouraging tissue growth in the case of a heart valve is to cover the surfaces of the valve with a knitted or woven cloth. However, cloth produced by current methods is limited in its durability and minimum thickness which can be achieved.

Flame spraying methods have also been attempted on metal heart valves and hip joints. In these methods a layer of particles is welded to a metal substrate by a spray of fused, minute droplets of metal. This procedure does not produce a desired uniformity of either porosity or thickness of coating. It generally produces very little porosity — only a rough surface. Also, objectionable oxide inclusions normally result. It is also difficult at best with these methods to coat small selected areas with good definition. A coating having a thickness equivalent to one layer of beads, which is often desired, is very difficult if not impossible to produce by flame spraying methods.

Sintering has also been attempted wherein beads of metal are applied in a slurry with binder. This, again, results in poor uniformity of coating thickness and selected area coverage is difficult.

Objects of the present invention are, therefore, to provide a porous metal coating of uniform and controlled thickness and porosity on a metal substrate, to provide a coating of the type described consisting of one or more layers of metal particles in which the original shape and size of the particles are retained, to provide such a coating free of objectionable oxides or binders, to provide such a coating with clear definition on small selected areas of a substrate, to provide such a coating for tissue ingrowth in metal prosthetic devices, and to provide an improved method for applying such a coating.

SUMMARY OF THE INVENTION

The present method intimately bonds a layer of porous metal to a metal substrate which for the present purpose is a prosthesis. The porous metal layer is more durable than cloth coverings, it can readily be made much thinner than cloth and it can more easily be limited to selected small areas, thereby providing a more appropriate medium for tissue ingrowth in a metal heart valve. Accurate control of the size and depth of the open cells makes the applied layer of porous metal appropriate to the biological interface desired for other applications in addition to heart valves where other types of tissue ingrowth are desired, such as the anchoring of the stem of an artificial hip, artificial knee, prosthetic limb, etc., to bone.

In carrying out the present method, the region of the metal substrate is cleaned, a suitable adhesive applied to the areas to be coated and appropriate metal powder sprinkled on. Additional layers of adhesive and powder can be applied to provide desired thickness. Pore size is determined by the size and shape of the particles in the powder and the degree of sintering in a sintering step which permanently attaches the particles to each other and to the substrate. The sintering operation is performed in a hydrogen atmosphere at a temperature near the melting point of the metal, the sintering being only sufficient to bond the particles, avoiding over-sintering which would close the porosity.

The invention will be better understood and additional objects and advantages will become apparent from the following description of the preferred embodiment illustrated in the accompanying drawings. Various changes may be made in the details of the method and certain features may be employed without others. All such modifications within the scope of the appended claims are included in the invention. The invention is not limited to prostheses.

BRIEF DESCRIPTION OF THE DRAWINGS

FIG. 1 is a sectional view of a heart valve made according to the invention;

FIG. 2 is a view on the line 2—2 in FIG. 1;

DESCRIPTION OF THE PREFERRED EMBODIMENT

Figure 3:
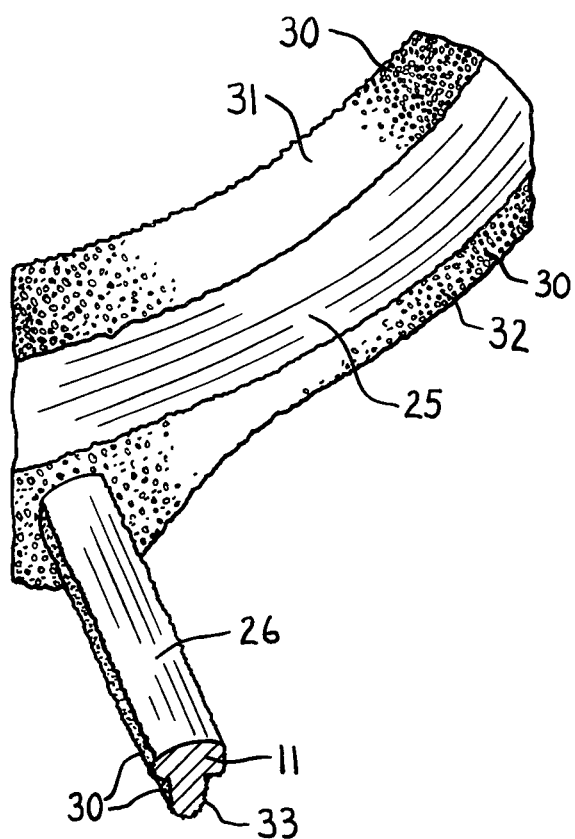
FIG. 3 is an enlarged view of the valve seat area in FIG. 1.

By way of example, the invention will be described in connection with the heart valve shown in FIG. 1. A circular orifice ring 10 is cast integrally with a plurality of cage struts 11 to confine a ball 12 in operative relation to the orifice ring. The orifice ring and cage struts are made of Stellite or other metal suitable for use in the blood circulatory system such as titanium, tantalum, stainless steel or Vitallium. Ball 12 may be made of metal or silicone rubber.

A sewing ring 15 provides means for suturing the valve permanently to the living tissue of the heart or aorta. For this purpose the present sewing ring comprises an insert 16 of suturable material such as silicone foam rubber or Teflon felt which imparts shape and body to the sewing ring. Insert 16 is enclosed in a tubular cloth sleeve 17 which is secured in a peripheral channel or groove 18 in orifice ring 10 by a spreader ring 19 and windings of thread 20. The ends of cloth sleeve 17 are folded back over the outer surface of insert 16 and sewed together with thread in a peripheral seam at 21. Other shapes and types of sewing ring may be used. The ball contact area 25 of ring 10 is polished and the ball contact area 26 on each cage strut 11 is similarly polished.

When the valve is installed in a heart or aorta, an ingrowth of connective tissue invades the mesh of cloth 17 and proceeds to encapsulate the sewing ring 15. This is desirable as it assists the sutures in securing and sealing the sewing ring to the heart or aorta tissue and it isolates the foreign body materials from the blood stream.

Such invading tissue also tends to advance over the bare metal surfaces of orifice ring 10 and cage struts 11. In earlier forms of heart valve the growth of tissue over the metal surfaces is undesirable because the tissue cannot obtain adherence or anchorage on the smooth metal. As the growth of tissue extends over the metal surfaces on the prior valves, pieces of tissue tend to break off and enter the blood stream with disastrous results to the patient.

Since the earliest forms of valves this problem has been alleviated by covering the major areas of the metal cage struts and orifice ring with cloth, leaving bare metal exposed only in minimum areas of ball contact on the cage struts and orifice ring. Such cloth coverings provide secure anchorage for the invading tissue and allow the inactive surfaces of the orifice ring and cage struts to become effectively encapsulated and isolated from the blood stream by a coherent and adherent layer of tissue from which pieces do not tend to break off and enter the blood stream.

The main objections to such cloth coverings involve the limitations of durability and thickness. Cloth coverings lack the desired durability and their thickness after encapsulation by body tissue reduces the cross sectional area of the passageway available for the free flow of blood. Also, in attempts to minimize the bare metal areas, more intricate and complicated structures were developed, making fabrication more difficult and expensive.

In the present form of construction secure anchorage is provided for invading and encapsulating tissue on selected metal surfaces by sintering on the metal surface a single layer of metal beads 30 which may or may not have the spherical shape represented in the drawings. On the orifice ring the exposed upstream surface 31 and exposed downstream surface 32 on opposite sides of the polished ball seating area 25 are covered with a layer of the beads 30. Similarly, on the cage struts 11 the outer surfaces 33 on opposite sides of polished surface 26 are covered with a layer of the beads 30.

The relative size of the beads is greatly exaggerated in FIGS. 1 and 2 to illustrate the principle of the invention. In practice, the beads are so fine that the thickness of a layer of beads is much less than the thickness of a layer of cloth. A very thin coating is desirable, the essential requirements being porosity and uniformity of coating. With inherent porosity and substantially perfect uniformity of coating there is no necessity for the present coating to be as thick as a layer of cloth as heretofore employed on the designated areas of the orifice ring and cage struts.

A novel method has been developed to apply the beads 30 to the selected areas to a uniform and controlled total thickness of coating and with uniform and controlled porosity. This method involves the treatment of the metal casting comprising orifice ring 10 and cage 11 before ball 12 has been inserted, before sewing ring 15 has been applied and before ball contact areas 25 and 26 have been polished. This metal casting will be referred to as a valve body or more generally as a substrate.

First, the valve body casting is thoroughly cleaned, preferably with a solvent and ultrasonic cleaning device. After drying, the areas 31, 32 and 33 which are to be covered with the beads 30 are painted with a suitable adhesive. An adhesive well adapted for this purpose is a mixture of Hycar Acrylic Latex 2600X146, manufactured by the B. F. Goodrich Chemical Co., in distilled water in the volumetric ratio of 1:3. Preferably, a few drops of food coloring are added to make the adhesive visible.

The adhesive is partially dried by blowing a gas over the casting. Then a second coat of adhesive is applied and dried to a tacky condition in the same manner. By painting the adhesive on with a brush, good definition of small areas is obtained.

Beads 30 are of the same metal as the valve body casting. In the present example, for use on a Stellite valve body casting, Stellite beads manufactured by Cabot Corporation, Stellite Division, of 200 to 325 mesh size are used. The beads are placed in a vial having a cap with a small hole approximately one-sixteenth inch in diameter. The beads are poured through the hole in the cap onto the adhesive covered portions of the orifice ring and cage casting until all the areas to be covered with porous metal are coated with the beads. The tacky adhesive holds essentially a single layer of the beads on the adhesive coated areas. Beads falling on non-painted areas 25 and 26 fall off without adhering.

To insure uniformity of coating, the bead-coated valve body is then blown with a gas to remove any beads in excess of the desired monolayer. The excess beads are dislodged by the gas stream while the monolayer is securely retained by the adhesive. Porosity is controlled in this step by the shape and size of beads selected, the beads being substantially uniform in size.

For other types of prostheses and for other purposes, multiple layers of particles may be desired and the particles in certain layers may be of different size and shape than in other layers. In such case, the first layer of particles is painted with adhesive, dried to tacky condition, and a second layer of particles is poured on and gas blown. This process may be repeated to provide the necessary thickness of coating, layer by layer. Thus, uniform controlled thickness is achieved regardless of the number of layers. Also, for some purposes the particles need not be of the same metal as the substrate.

The bead-coated valve body is placed in a suitable sintering furnace and sintered. This may be done in the following manner using a vacuum furnace having Tungsten heating elements and sighting ports for observation of the sintering operation. The furnace chamber is evacuated, filled with hydrogen to about one atmosphere of pressure and re-evacuated. This is repeated three times and, finally, evacuation is continued at room temperature until the pressure in the chamber is less than one micron.

For sintering, current to the heater is turned on and gradually increased until the heated zone is approximately 700° to 900° C., normally requiring about 15 to 20 minutes. Hydrogen is then admitted to the furnace chamber until the pressure is approximately one-half atmosphere. Then current to the heater is gradually increased until the temperature of the valve body is approximately 1300° C., as determined by sighting the valve body with an optical pyrometer, this step normally requiring 10 to 15 minutes. The valve body is allowed to remain at this temperature for one hour. In the absence of oxygen, no oxides are formed.

At that time the temperature is gradually decreased over a period of 20 to 30 minutes until the furnace is back to room temperature. Then the hydrogen atmosphere is pumped out of the furnace chamber, the chamber filled with air and the valve body removed. Alternatively, the temperature could be reduced from the sintering temperature to about 850° C., the hydrogen pumped out and the chamber then cooled to room temperature in a vacuum.

Coating and polishing steps follow the sintering operation just described. To prevent the lodging of polishing compound into the porous metal coating, the valve body is temporarily coated with a suitable material to fill the pores prior to polishing. By way of example, the coating step is carried out by dipping the valve body in a twenty percent solution of polyvinylpyrolodone. The valve body is dried at 80 ° to 90° C. Preferably, the coating and drying steps are repeated two more times.

Ball contact areas 25 and 26 are polished. To remove the temporary coating which was applied prior to the polishing step, the polished valve body is placed in distilled water in an ultrasonic cleaner for a sufficient interval, such as twenty minutes. This cleaning step is repeated with fresh distilled water until all the polyvinylpyrolodone is removed from the valve body. In a final step the valve body is immersed in methanol in an ultrasonic cleaner for twenty minutes. After drying in a stream of gas, the valve body is ready for application of sewing ring 15 and insertion of ball 12.

Figure 4:
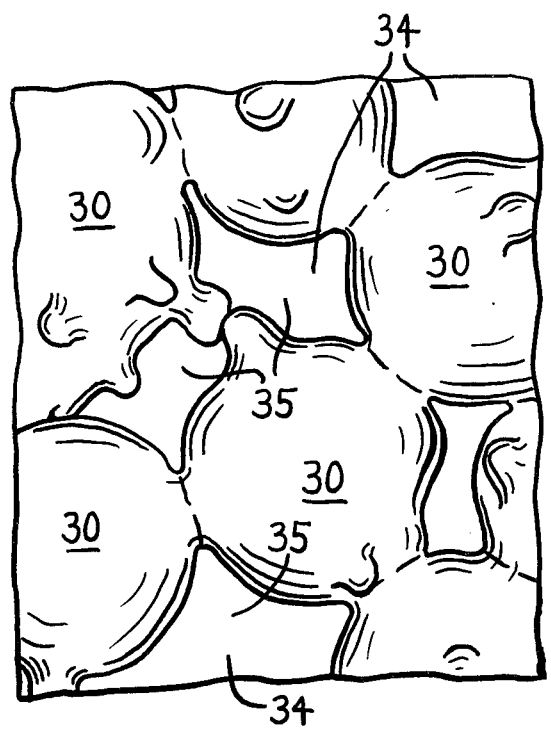
FIG. 4 is an elevation view showing the porosity of the beaded surface at a magnification of 550X.

Fig. 3 is a drawing made from a photograph at an enlargement of 10X showing the three surfaces 31, 25, 32 in FIG. 1. FIG. 4 is a drawing made from a photograph at an enlargement of 550X showing the porosity available for ingrowth of living tissue in a substantial monolayer of beads 30 on a substrate 34.

In the absence of physical pressure and with proper control of the sintering temperature and time, the beads are bonded to each other and to the substrate without gross deformation, leaving intercommunicating openings 35 around the beads for the ingrowth of body tissue. When the sintered coating consists of multiple layers of beads, the openings 35 extend through the thickness of the coating from the surface down to the substrate. The sintering operation also controls the porosity.

The present method is applicable to any sinterable combination of metals. For some purposes the beads, or non-spherical particles, may be larger than the size range described herein for heart valves.

Figure 5:
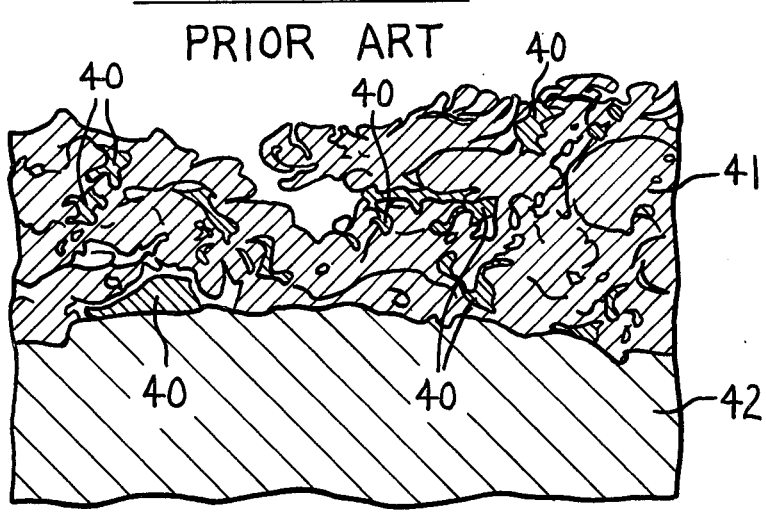
FIG. 5 is a drawing made from a photomicrograph at a magnification of 300X, showing a cross section of a conventional flame sprayed coating.

Attempts to produce a porous metal surface by flame spraying (shupping) and like methods have not produced the desired results. FIG. 5 is a drawing made from a photomicrograph at an enlargement of 300X showing a cross section of a flame sprayed coating. The coating is rough but not uniformly porous and not of uniform thickness. In fact, very little porosity is evident. Also, there are objectionable oxide inclusions as indicated at 40 in the coating 41 applied to substrate 42. By such methods it is difficult at best to coat selected areas with good definition and a porous coating equivalent to one layer of beads would be very difficult, if not impossible, to produce.

Flame spraying according to the Hahn U.S. Pat. No. 3,605,123 is subject to the same disadvantages described above in connection with FIG. 5.

When beads are applied in a slurry with a binder according to prior art teachings, it is found that the coating uniformity is poor and selected area coverage is difficult. Uniform coverage of selected areas in one or multiple controlled layers with spherical or non-spherical beads retaining the controlled porosity provided by the original shape and size of the particles has not been achieved by any of the prior art methods.

Having now described our invention and in what manner the same may be used, what we claim as new and desire to protect by Letters Patent is:

1. A heart valve having a metal orifice ring and cage struts confining a movable valve member, said valve member in closed position seating on a contact area of said orifice ring and in moving between closed and open positions engaging contact areas on said cage struts, said orifice ring and cage struts having surfaces exposed to a blood stream flowing through the valve and subject to the growth of connective tissue on said surfaces and a porous metal coating of controlled porosity and thickness sintered on said exposed metal surfaces other than said valve member contact areas to promote the ingrowth of said tissue so as to anchor the tissue to the metal in selected areas and prevent said tissue from breaking off and entering the blood stream, said coating comprising substantially a monolayer of sinterable metal particles of substantially uniform size and shape adhered to said selected areas and sintered on said selected areas, said particles being bonded to said arifice ring and cage struts and to each other without gross deformation of the particles so as to leave intercommunicating openings around the particles for said ingrowth of tissue.

2. A heart valve as defined in claim 1 including a second discrete monolayer of metal particles of substantially uniform size and shape sintered on said first monolayer without gross deformation of the particles so as to leave intercommunicating openings around the particles extending through the thickness of the coating.

3. A heart valve as defined in claim 2 wherein the particles in said second monolayer are of substantially the same size and shape as the particles in said first monolayer.

4. A heart valve as defined in claim 2 wherein the particles in said second monolayer have a different size or shape than the particles in said first monolayer.

* * * * *